United States Patent [19]

Harman, III

[11] 4,272,486
[45] Jun. 9, 1981

[54] INTERFERENCE REACTOR TO PROVIDE SELECTIVE SO₂ MEASUREMENT BY FLUORESCENT METHODOLOGY

[75] Inventor: John N. Harman, III, Placentia, Calif.

[73] Assignee: Beckman Instruments, Inc., Fullerton, Calif.

[21] Appl. No.: 12,174

[22] Filed: Feb. 14, 1979

[51] Int. Cl.³ .................. G01N 21/64; G01N 21/33
[52] U.S. Cl. .................... 422/91; 23/232 R; 23/232 E; 55/73; 73/23; 250/373; 250/461 R; 422/101
[58] Field of Search .............. 23/232 R, 232 E; 422/88, 91, 101; 73/23; 250/373, 461 R; 55/73

[56] References Cited

U.S. PATENT DOCUMENTS

| 2,134,543 | 10/1938 | Andrews . | |
| 2,180,353 | 11/1939 | Foster . | |
| 2,474,001 | 6/1949 | Levine . | |
| 2,510,803 | 6/1950 | Cooper | 252/464 |
| 2,785,141 | 3/1957 | Fleck | 252/464 |
| 3,207,703 | 9/1965 | Innes et al. | 256/455 |
| 3,300,516 | 1/1967 | Vrbaski . | |
| 3,547,587 | 12/1970 | Innes | 23/232 E |
| 3,795,812 | 3/1974 | Okabe | 250/373 |
| 4,077,774 | 3/1978 | Neti et al. | 23/232 R |

Primary Examiner—Ronald Serwin
Attorney, Agent, or Firm—Robert J. Steinmeyer; Paul R. Harder; Edward C. Jason

[57] ABSTRACT

In a sulfur dioxide analyzer which measures the content of sulfur dioxide by fluorescence of sulfur dioxide molecules when illuminated by an ultraviolet light source, there is disclosed a converter containing vanadium pentoxide for removal of polynuclear aromatic hydrocarbons which produce interference when sulfur dioxide is measured by fluorescent methodology.

14 Claims, 8 Drawing Figures

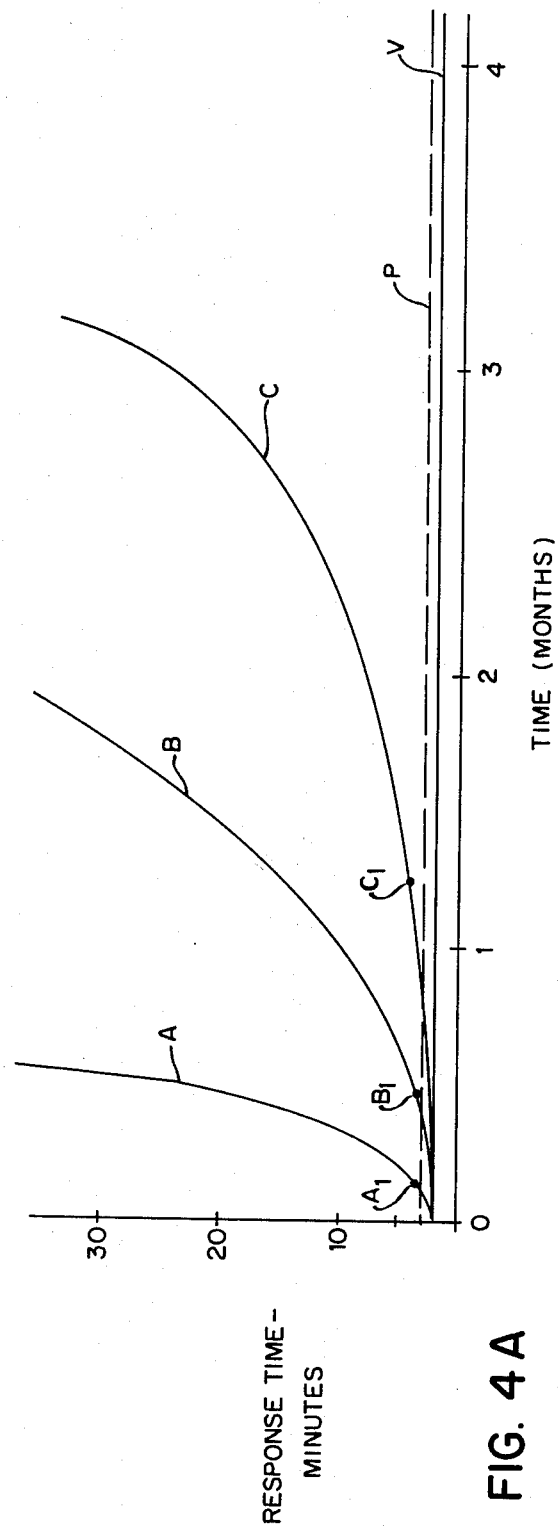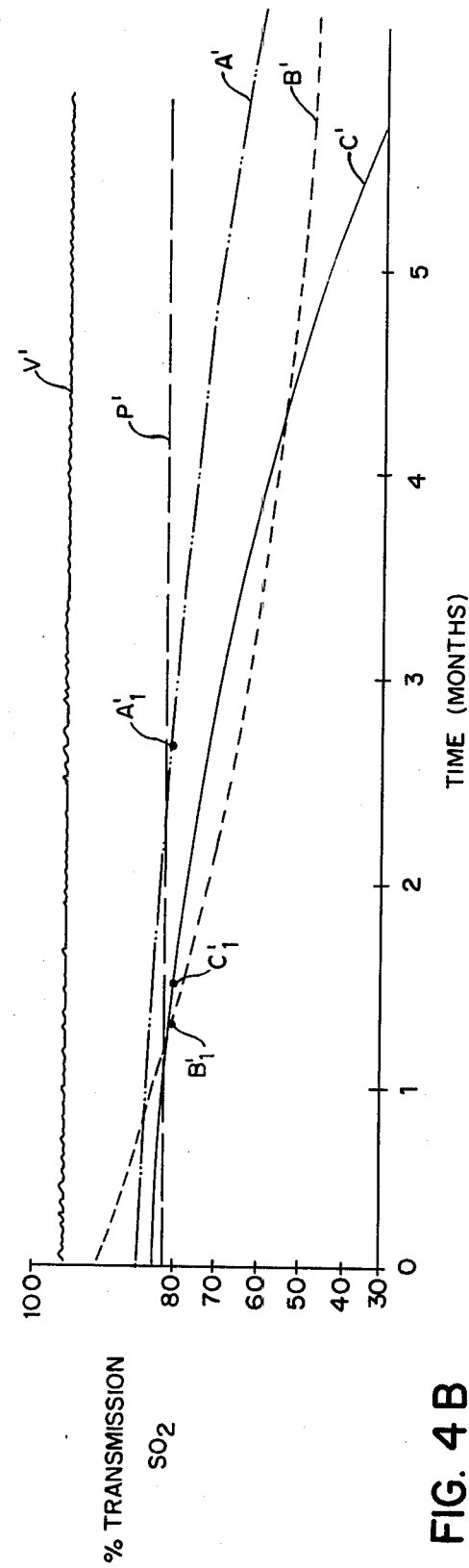

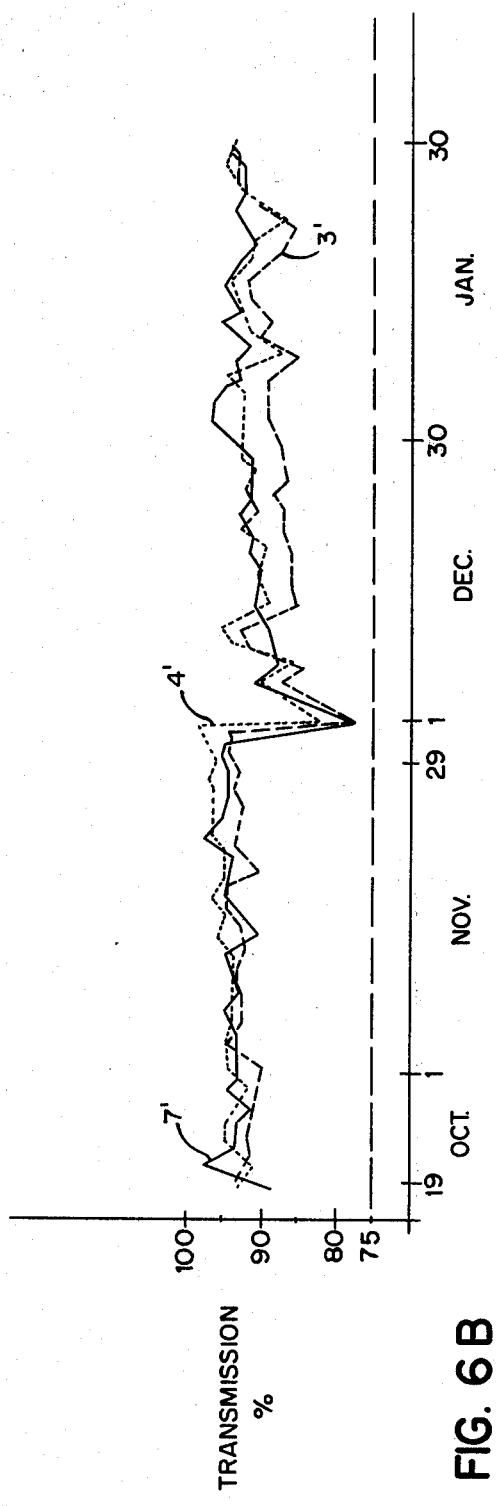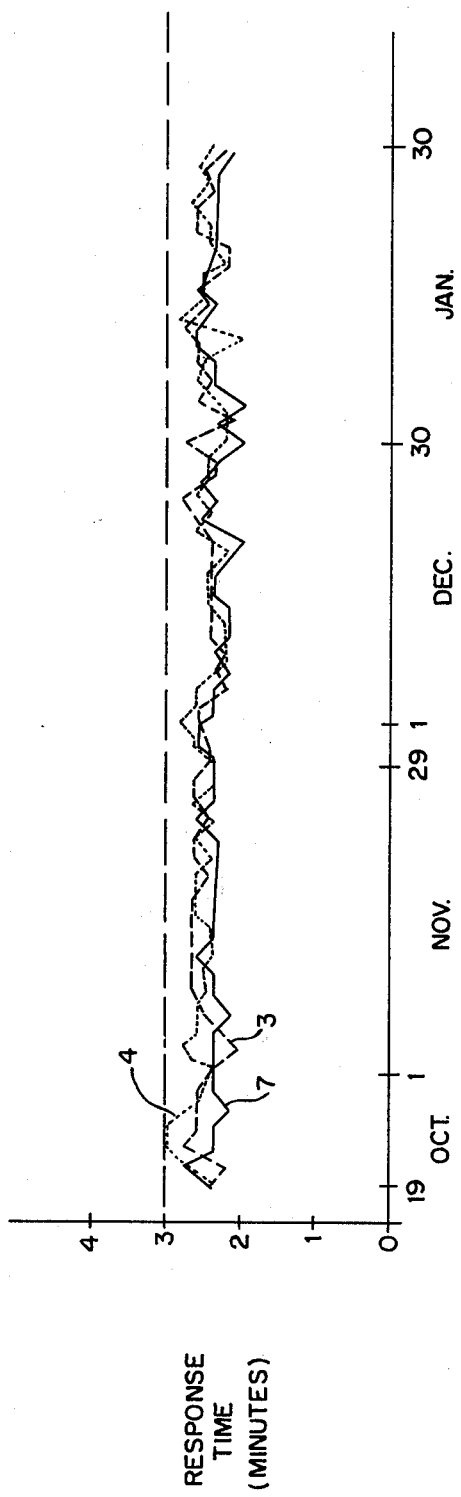
FIG. 6B
FIG. 6A

INTERFERENCE REACTOR TO PROVIDE SELECTIVE SO₂ MEASUREMENT BY FLUORESCENT METHODOLOGY

BACKGROUND OF THE INVENTION

In sulfur dioxide analyzers, the sample input stream containing sulfur dioxide to be analyzed is presented to a reaction chamber in which it is illuminated by an ultraviolet light source. Sulfur dioxide molecules present absorb the incident radiation, increase in energy content momentarily and then release the absorbed energy at a longer wavelength than the incident radiation (fluorescence). The fluorescence radiation is detected at right angles to the incident radiation by a blue light sensitive photomultiplier tube and electrically amplified to be displayed as a signal proportional to the concentration of sulfur dioxide present in the input gas sample. Further details of fluorescent methodology may be found disclosed in U.S. Pat. No. 3,795,812 to Hideo Okabe.

Other compounds exist in the polluted air which also fluoresce in a similar fashion to that fluorescence exhibited by sulfur dioxide. Polynuclear aromatic hydrocarbons (such as napthalene, anthracene, phenanthracene, etc.) are the principal class of organic compounds which exhibit this behavior. Characteristics required of a polynuclear aromatic hydrocarbon removing reactor are that it pass a relatively constant and high percentage of the sulfur dioxide (at part per million levels) presented to it, that it add no appreciable time constant to that inherent within the instrument, that any added response time is relatively constant in time and that it effectively convert polynuclear aromatic hydrocarbons, such as napthalene, the typical test compound, to a non-interfering substance.

Prior art discloses two methods for removing the polynuclear aromatic hydrocarbon interference.

The first method is ozone oxidation of the polynuclear aromatic hydrocarbons by means of an ultraviolet light (or the equivalent photolysis of the polynuclear aromatic hydrocarbons with the incident ultraviolet energy). This approach has several problems among which are (1) the system is humidity dependent, (2) there is a possibility of conversion of SO₂ to SO₃, (3) the system is expensive, and (4) the system is dangerous.

The first listed problem is that ozone conversion is humidity dependent. As the sample gas stream rises in humidity, the effectiveness of ozone in the polynuclear aromatic compound oxidation process is greatly changed. The second problem is that the presence of ozone (O₃), with its tendency to oxidize its surroundings, presents the problem of converting sulfur dioxide to sulfur trioxide as in the formula below.

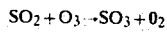

$$SO_2 + O_3 \rightarrow SO_3 + O_2$$

Sulfur trioxide does not exhibit the same fluorescence that sulfur dioxide exhibits, thus, the measurement of sulfur dioxide is diminished. The third problem involves not only equipment used to generate ozone but also the equipment adapted for use with ozone due to its highly corrosive nature. Equipment to produce and be used with ozone is extremely expensive since it must be fabricated of corrosion resistant materials. The fourth problem is that operation with ozone is extremely dangerous. This is also due to its highly corrosive nature and the fact that ozone (O₃) is extremely toxic.

A second possible solution to the problem of polynuclear aromatic hydrocarbon interference is the thermal oxidation of the interfering polynuclear aromatic hydrocarbons by passage of the gas sample stream through heated amorphous graphite in order to convert them to noninterfering species. While the use of an amorphous graphite converter eliminated the problems inherent in the ozone oxidation system, it presented problems of its own. Amorphous graphite will produce inconsistent transmission percentages and response times from production lot to production lot. These inconsistencies will exist within the same production lot due to variations in size, surface area and trace impurities. Furthermore, the amorphous graphite had the additional problem of being consumed over the space of several months. While the shortened life of the amorphous graphite presented a small problem, the major problem exists in the fact that the response time of the converter degrades to unacceptable levels in a short time and that it is not a repeatable material, that it will not produce the same response from filling to filling, requiring a total recalibration every time the amorphous graphite is consumed. Possible solutions to the problems inherent with the use of amorphous graphite have not been disclosed in prior art. Although removal of polynuclear aromatic hydrocarbons with catalysts is both a theoretical and practical possibility, oxidative catalysts such as vanadium pentoxide were considered unsuitable because of the possibility of sulfur dioxide loss due to conversion to sulfur trioxide by oxidation. These catalysts, including vanadium pentoxide, were thought to convert sulfur dioxide to sulfur trioxide, which does not fluoresce as sulfur dioxide does. Thus, oxidizing catalysts were eliminated as a possible solution to the problem of polynuclear aromatic hydrocarbon interference in measuring sulfur dioxide by fluorescent methodology.

It is therefore an object of the present invention to provide apparatus for removal of polynuclear aromatic hydrocarbons which is repeatable in nature.

It is also an object of the present invention to provide an apparatus for removal of polynuclear aromatic hydrocarbons which is inexpensive.

It is a further object of the present invention to disclose apparatus for removal of polynuclear aromatic hydrocarbons which is relatively safe.

It is also a further object of the present invention to disclose apparatus for removal of polynuclear aromatic hydrocarbons which will not interfere with the measurement of a constituent of interest in a sample gas stream.

SUMMARY OF THE INVENTION

The present invention avoids the deficiencies of being humidity dependent, possible conversion of input sulfur dioxide to sulfur trioxide, the expense of prior art systems, the dangerous processes of prior art systems and the inconsistency of prior art systems used in the removal of polynuclear aromatic hydrocarbons from a sample gas stream. The present invention comprises a converter which is disposed in a sample-stream prior to a fluorescent method measuring device. The converter is heated to approximately 400° C. and contains vanadium pentoxide mixed with sand to remove polynuclear aromatic hydrocarbon interference. Furthermore, the present invention passes a relatively constant and high percentage of sulfur dioxide, it adds no appreciable time constant to that inherent within the instrument, any added response time is relatively constant and it effectively converts polynuclear aromatic hydrocarbons to non-interfering species.

BRIEF DESCRIPTION OF THE DRAWINGS

FIGS. 4A and 4B are graphical representations illustrating the response time and transmission percentage for the present invention compared to prior art converters.

FIGS. 6A and 6B are graphical representations of long term test results of the present invention.

DESCRIPTION OF THE PREFERRED EMBODIMENT

Figure 1:
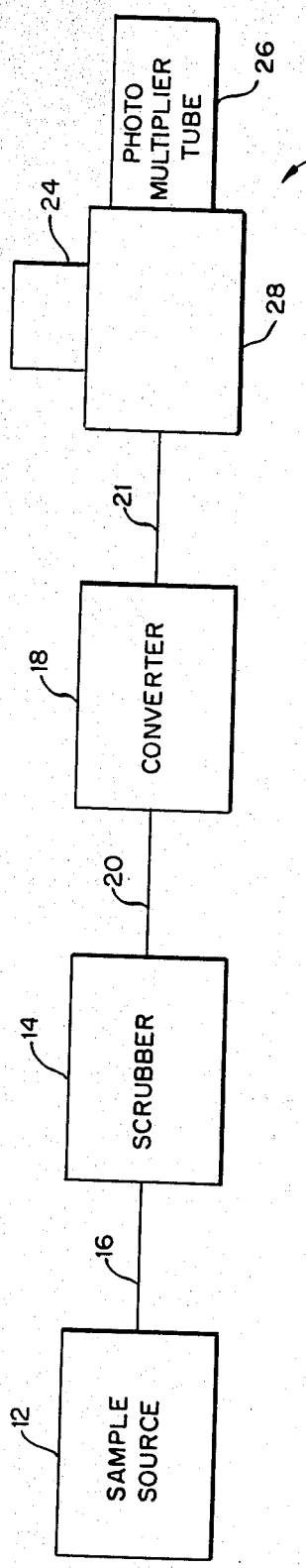
FIG. 1 is a block flow diagram illustrating the use of the present invention.

FIG. 1 illustrates a sample source 12 connected to a scrubber 14 through a conduit 16. Scrubber 14 is connected to a converter 18 through a conduit 20. Converter 18 is connected through conduit 21 to a fluorescent measuring device 22 having an ultraviolet source 24 and a photomultiplier tube 26 connected to a housing 28.

In actual operation, sample source 12 supplies a source of sample gas for which the concentration of sulfur dioxide is to be measured through conduit 16 to scrubber 14. Scrubber 14 is typically a housing containing a mixture of mercuric chloride with Teflon to remove hydrogen sulfide and various mercaptans. Mercaptans, such as $C_2H_5SH$ and other sulfur containing species such as $H_2S$ will produce sulfur dioxide when combined with oxygen under heat which will increase the sulfur dioxide reading. Once hydrogen sulfide and mercaptans are removed by scrubber 14 the sample gas stream is then passed to converter 18 through conduit 20. Converter 18 was typically, in prior art, a housing containing amorphous graphite heated to approximately 400° C. The amorphous graphite of converter 18 had many problems, such as inconsistency in tramission and response (see FIGS. 4A and 4B), a short life time and various variations in size, surface area and trace impurities. The present invention, as will be described in detail in connection with FIG. 2, contains vanadium pentoxide heated to about 400° C. to remove the polynuclear aromatic hydrocarbons. Polynuclear aromatic hydrocarbons "fluoresce" or give off light in the same wavelength region as sulfur dioxide when excited by ultraviolet light. This property results in polynuclear aromatic hydrocarbons indicating either the presence of or a greater quantity of sulfur dioxide than is in fact present. When the primary sources of interference, namely hydrogen sulfide, mercaptans and polynuclear aromatic hydrocarbons have been removed, the sample gas stream is then passed to fluorescent measuring device 22 through conduit 21. Fluorescent measuring device 22 comprises an ultraviolet source 24 which produces incident ultraviolet rays on the gas sample to be measured in housing 28. Sulfur dioxide molecules absorb the incident radiation, increase in energy content momentarily and then release the absorbed energy at a longer wavelength than the incident radiation. The fluorescent radiation is detected by photomultiplier tube 26 and is electrically amplified to be displayed as a signal proportional to the concentration of sulfur dioxide present in the input gas sample.

Figure 2:
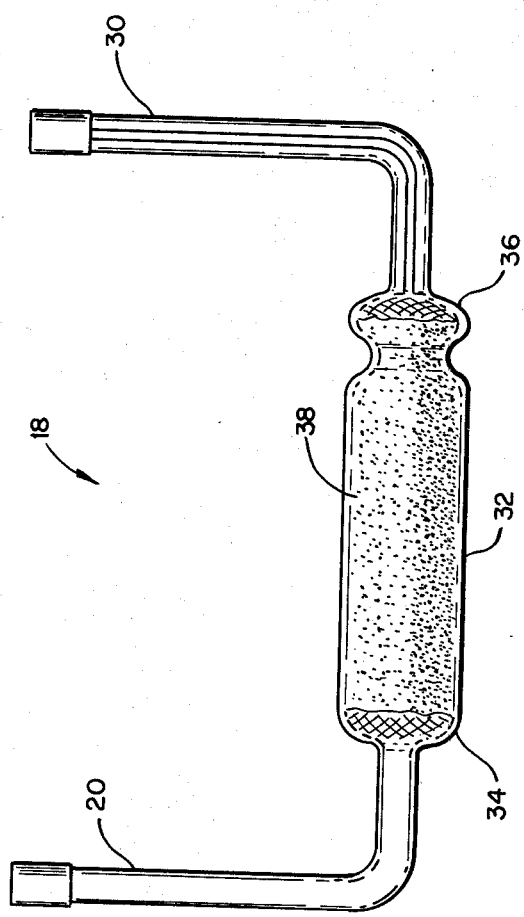
FIG. 2 is a plan view of the present invention.

Referring now to FIG. 2, converter 18 is illustrated as comprising a housing 32 containing a reactant, preferably vanadium pentoxide, mixed with an inert, high temperature material, preferably sand, and having disposed therein fibrous material plugs 34 and 36 to prevent loss of vanadium pentoxide mixed with sand as shown at 38. Housing 32 may be of any construction, however, a quartz tube capable of withstanding high temperatures such as 400° C. is preferred. Prior art converters have used amorphous graphite with problems of inconsistency of transmission percentage and response time; however, vanadium pentoxide mixed with sand is preferred as more consistent (see FIGS. 4A and 4B). Fibrous material 34 and 36, may be any gas permeable, solid impermeable material, however, quartz fiber pads or fiberglass fibers are preferred, due to their heat resistance.

Figure 3:
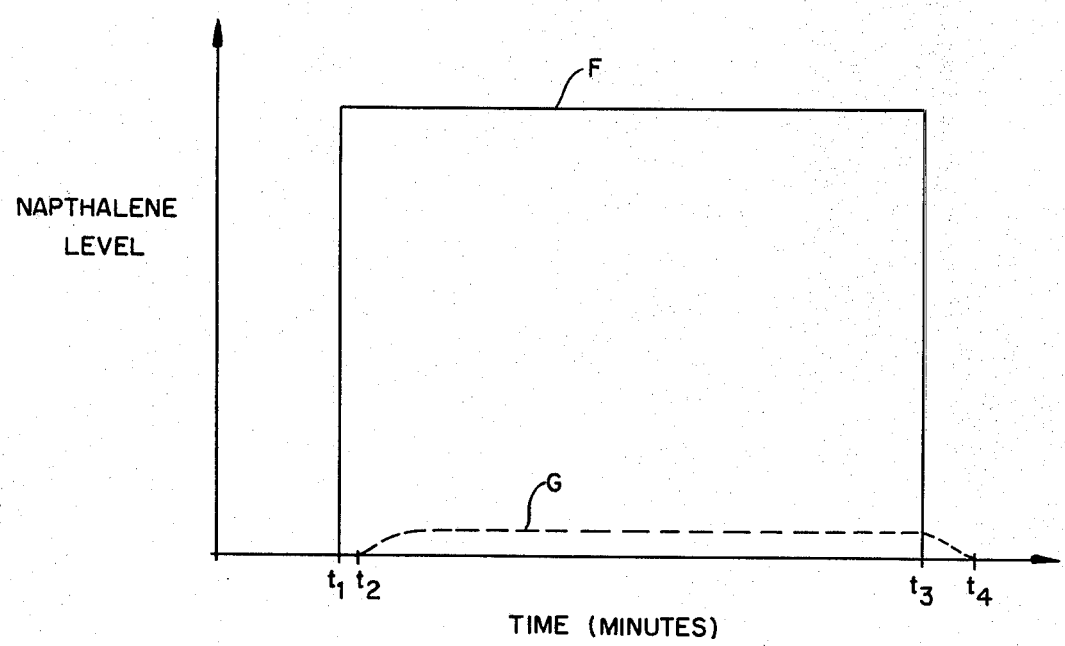
FIG. 3 is a graphical representation of the transmission of napthalene through the present invention.

FIG. 3 illustrates the rejection characteristics of the present invention for a typical polynuclear aromatic hydrocarbon test gas such as napthalene. Curve F represents an input pulse of napthalene increasing to its maximum representing a quantity of napthalene that will produce an indication of 0.1 ppm concentration of sulfur dioxide at time $t_1$. The input pulse maintains this maximum until time $t_3$ where it decreases to its minimum by removal of the napthalene source from the input of a fluorescent sulfur dioxide analyzer. Dotted curve G represents the response of a fluorescent sulfur dioxide analyzer when the same input pulse of napthalene is presented to its input through a converter according to the present invention. Dotted curve G increases to its maximum at time $t_2$ which represents an indication of 0.005 ppm sulfur dioxide by the fluorescent sulfur dioxide analyzer. Curve G continues at this maximum until time $t_4$ where it slowly decreases to zero. The time delays between time $t_1$ and time $t_2$ and between times $t_3$ and $t_4$ are due to the transmission time lag added by the converter between the napthalene source and the fluorescent sulfur dioxide analyzer. Spectrochemical analysis of various samples indicated that in general samples with higher vanadium pentoxide content functioned with better napthalene rejection than samples with lower vanadium pentoxide levels. Further experimentation, wherein the mixture shown at 38 of FIG. 2 was doped with varous levels of vanadium pentoxide, revealed that part per million hours of polynuclear aromatic hydrocarbon rejection were directly related to the amount of vanadium pentoxide present in the converter. The tests indicated that increasing levels of vanadium pentoxide increased the napthalene rejection while not affecting significantly the sulfur dioxide transmission; however, optimum results are achieved by a mixture of sand and two percent by weight vanadium pentoxide as described in conjunction with FIG. 5. Transmission of sulfur dioxide through vanadium pentoxide is contra to the expected results since vanadium pentoxide is believed to be a good catalyst for conversion of sulfur dioxide to sulfur trioxide or other non-fluorescing species.

Referring now to FIGS. 4A and 4B, graphical representations of response time and percent transmission, both plotted as a function of time, are illustrated for amorphous graphite converters and a vanadium pentoxide converter. FIG. 4A illustrates four curves, A, B and C characterizing a typical response time plotted over a several month period of three samples of amorphous graphite from the same production lot and curve V which characterizes the response time of a mixture of vanadium pentoxide and sand. Dotted line P represents the maximum acceptable response time, three minutes. Curve A, indicating the performance of graphite sample A, indicates that graphite sample A had an extremely short response time life. As indicated by point $A_1$, the response time of graphite sample A increased above the acceptable limit of three minutes within a week. Curve B, for graphite sample B, indicates that the response time remained within the acceptable three minute limit for a longer period, that is almost two weeks, as indicated by point $B_1$ on curve B. Curve C for graphite sample C indicates that graphite sample C had a response time life of approximately a month and a quarter prior to substantially exceeding the acceptable limit of three minutes as indicated by point $C_1$ on curve C. Curve V illustrates that the response time life for a mixture of vanadium pentoxide and sand greatly exceeded that of the three graphite samples. In fact, the mixture of vanadium pentoxide and sand remained well within the three minute acceptable time limit for the entire four month duration of the test.

FIG. 4B illustrates the percent transmission of sulfur dioxide through four converters, A', B', and C' representing percent transmission of the same three samples of amorphous graphite illustrated in FIG. 3A and curve V' representing percent transmission of sulfur dioxide of the same mixture of vanadium pentoxide and sand as illustrated in FIG. 3A. An acceptable limit of percent transmission of sulfur dioxide is approximately 80% as indicated by dotted line P'. As can be seen by curve A', graphite sample A fell below the acceptable limit of 80% transmission in a little under three months as indicated by point $A'_1$ of curve A'. Graphite sample B showed a drop below the acceptable limit of 80% in slightly over a month as indicated by point $B'_1$ of curve B'. Graphite sample C fell below the acceptable limit of 80% after approximately one and one-half months as indicated by point $C'_1$ of graph C'. The percent transmission of sulfur dioxide remained well above the 80% limit for a converter filled with vanadium pentoxide and sand for the entire period of the test as indicated by curve V'.

As can be seen in the graphical representations 4A and 4B, the response time of amorphous graphite samples increased to an unacceptable limit within the space of two months, whereas vanadium pentoxide maintains a short response time with no degradation for a period of at least twice as long. Also, the percent transmission of sulfur dioxide falls below acceptable limits for the graphite samples rather rapidly, whereas the percent transmission for vanadium pentoxide and sand is maintained at a very high level with minimum degradation.

Figure 5:
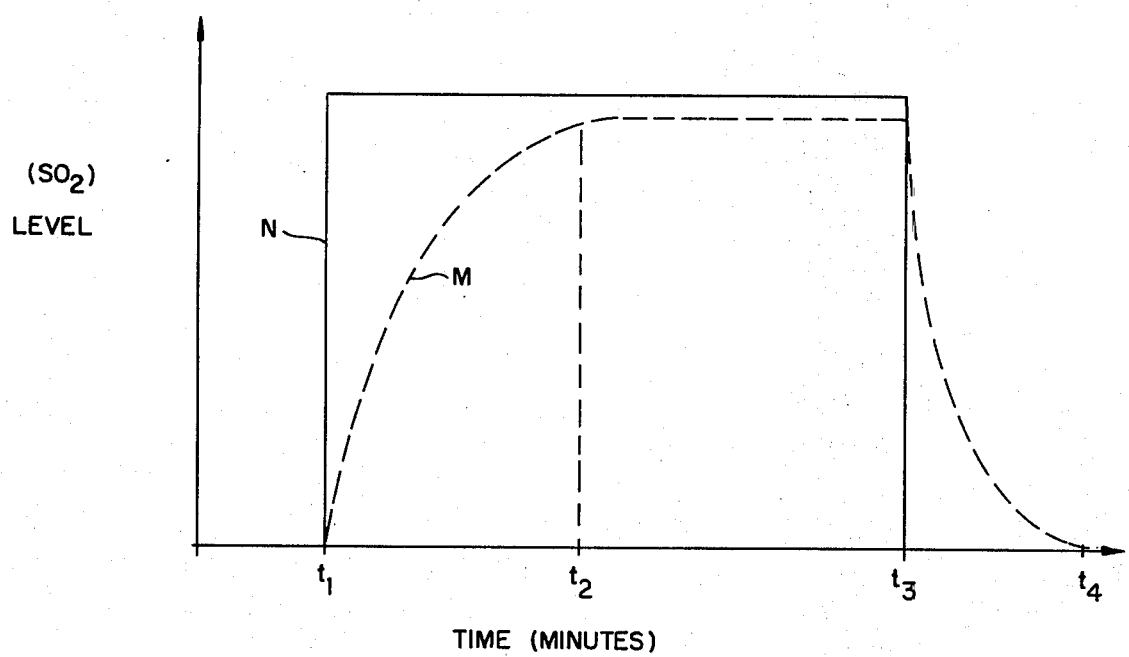
FIG. 5 is a graphical representation of a comparison between test stimulus and response of the present invention.

FIG. 5 is a graphical representation of a typical characterization of a sulfur dioxide input of 1.0 ppm without a converter and with a vanadium pentoxide mixed with sand converter. The solid step function N of FIG. 5 represents the variation in concentration of sulfur dioxide at the input to a fluorescent sulfur dioxide analyzer. At time $t_1$ the step function increases to its maximum of 1.0 ppm sulfur dioxide and continues at this level until time $t_3$ when the sulfur dioxide source is removed from the input to the fluorescent sulfur dioxide analyzer. Dotted line M beginning at time $t_1$ represents the performance of the fluorescent sulfur dioxide analyzer equipped with a test converter when it is subjected to a step function sulfur dioxide input as illustrated by step function N between times $t_1$ and $t_3$. At time $t_1$ dotted line M increases until a maximum is reached at time $t_2$. Dotted line M then continues at this maximum to time $t_3$ when the sulfur dioxide source is removed from the input of the fluorescent sulfur dioxide analyzer. At this point curve M slowly decreases to zero at time $t_4$. The time delay between time $t_1$ and $t_2$ is the response time plotted for the converter being tested. The ratio between one ppm and the maximum attained by dotted curve M represents the percent transmission of the converter being tested. For this particular example the percent transmission was approximately 95% and the response time was approximately 2½ minutes.

Additional test data for several vanadium pentoxide converters is illustrated in FIG. 6B as curves 3', 4', and 7' indicating percent transmission and in FIG. 6A as curves 3, 4 and 7 indicating response time. Curves 3, 3' and 7 and 4', 4 and 7' are representative of test data obtained from a group of converters which were tested. The upper portion of the axis indicates the percent transmission of sulfur dioxide for converters filled with a mixture of 2% by weight vanadium pentoxide and sand while the lower portion indicates the response time in minutes; both are plotted over a period of months. This test data was generated by a process similar to that described in connection with FIG. 5 wherein a Beckman Model 953 Sulfur Dioxide Analyzer was calibrated from a permeation tube source of sulfur dioxide having a known sulfur dioxide output per unit of time, certified by the National Bureau of Standards. The test converter assembly is placed in line between the source of known sulfur dioxide concentration and the sulfur dioxide analyzer. A response time curve for the converter is generated by the measurement data accumulated by a potentiometric recorder connected to the sulfur dioxide analyzer output. A typical characterization of a sulfur dioxide input from the sulfur dioxide source has been illustrated as curve N of FIG. 5.

The testing was performed once every several days to establish the functionality of the converter after a given time period. Between test periods, the converter of the present invention was operated in one of two groups. One group was operated with a continuous flow of ambient air at the converter's normal flow rate. The second group was operated with a continuous flow of ambient air doped to the approximately 0.05 ppm sulfur dioxide level at the converter's normal flow rate.

The results of extensive experimentation demonstrated that a mixture of 2% vanadium pentoxide by weight and sand produced optimum percent transmission results and, as such, comprises the preferred embodiment. However, 0.2 to 20% vanadium pentoxide and sand or additional high temperature inert mixing agents such as quartz or glass beads may be used. In the alternative, a bed of vanadium pentoxide without an inert material may be used, but excessive pressure drops and restricted flow may be anticipated.

Repetition of the tests described in conjuction with FIGS. 3 and 5 demonstrated the following: (1) excellent transmission of sulfur dioxide through a heated bed of vanadium pentoxide mixed with sand was shown; (2) excellent napthalene rejection is shown over long periods of time with no apparent degradation in napthalene rejection capability; (3) by making a mixture of vanadium pentoxide and sand, the response time through the converter does not degrade from acceptable behavior;

(4) the expected life of the system (part per million hours of adequate napthalene rejection) is at least several fold better than a graphite system; (5) much more consistency of converter behavior is possible since inconsistencies within production lots is eliminated by the use of vanadium pentoxide.

The foregoing description of the preferred embodiment is shown by way of example only and is not to be considered as limiting, since many variations may be made by those skilled in the art without departing from the scope or spirit of the invention which is to be construed only in light of the following claims.

What is claimed is:

1. A converter for removing polynuclear aromatic hydrocarbons from the sample gas stream of a fluorescent gas analyzer, without substantial effect upon any sulfur dioxide contained in said sample gas stream, comprising:

housing means having an inlet for receiving a sample gas stream and an outlet for exhausting said sample gas stream;

a mixture of vanadium pentoxide and an inert material disposed within said housing means to contact said sample gas stream; and means adjacent said inlet and said outlet to prevent loss of said vanadium pentoxide.

2. A converter according to claim 1 wherein said mixture comprises two percent vanadium pentoxide by weight.

3. A converter according to claim 1 wherein said inert material is sand.

4. A converter according to claim 1 wherein said fibrous material means comprise quartz fiber pads.

5. A converter according to claim 1 wherein said fibrous material comprises fiberglass plugs.

6. A converter according to claim 1 wherein said housing means comprises a quartz glass tube.

7. In a system for measuring the sulfur dioxide content of a sample gas stream utilizing a fluorescent gas analyzer, the improvement comprising:

housing means having an inlet and an outlet disposed between a source of sample gas and said fluorescent analyzer, said housing means containing vanadium pentoxide to contact said sample gas for removing polynuclear aromatic hydrocarbons.

8. The improvement of claim 7 further including an inert material co-mingled with said vanadium pentoxide.

9. The improvement according to claim 8 wherein said inert material is sand.

10. The improvement according to claim 8 wherein said inert material co-mingled with said vanadium pentoxide comprises a mixture of two percent by weight vanadium pentoxide.

11. The improvement according to claim 7 further including fibrous plugs disposed within said housing means at said inlet and said outlet to prevent loss of said vanadium pentoxide.

12. The improvement according to claim 11 wherein said fibrous plugs comprise quartz fiber plugs.

13. The improvement according to claim 11 wherein said fibrous plugs comprise fiberglass plugs.

14. In a system having a sample gas source and a fluorescent analyzer, the method for removing polynuclear aromatic hydrocarbons comprising the steps of:

placing a housing means containing vanadium pentoxide between said sample gas source and said analyzer;

contacting said sample gas with said vanadium pentoxide; and exhausting said sample gas to said analyzer.

* * * * *